(12) United States Patent
Plumptre et al.

(10) Patent No.: US 10,201,663 B2
(45) Date of Patent: Feb. 12, 2019

(54) ASSEMBLY FOR A DRUG DELIVERY DEVICE

(71) Applicant: SANOFI-AVENTIS DEUTSCHLAND GMBH, Frankfurt am Main (DE)

(72) Inventors: David Aubrey Plumptre, Worcestershire (GB); Robert Frederick Veasey, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/770,852

(22) PCT Filed: Mar. 10, 2014

(86) PCT No.: PCT/EP2014/054521
§ 371 (c)(1),
(2) Date: Aug. 27, 2015

(87) PCT Pub. No.: WO2014/139910
PCT Pub. Date: Sep. 18, 2014

(65) Prior Publication Data
US 2016/0008551 A1    Jan. 14, 2016

(30) Foreign Application Priority Data
Mar. 11, 2013 (EP) ..................... 13158512

(51) Int. Cl.
*A61M 5/315* (2006.01)
(52) U.S. Cl.
CPC .... *A61M 5/31541* (2013.01); *A61M 5/31555* (2013.01); *A61M 5/31585* (2013.01);
(Continued)

(58) Field of Classification Search
CPC ............ A61M 5/3146; A61M 5/31551; A61M 5/31595; A61M 5/31501; A61M 5/31528;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 102083487 | 6/2011 |
| EP | 0937471 | 8/1999 |

(Continued)

OTHER PUBLICATIONS

International Search Report for Int. App. No. PCT/EP2014/054521, completed Apr. 29, 2014.
(Continued)

*Primary Examiner* — Emily Schmidt
(74) *Attorney, Agent, or Firm* — Fish & Richardson P.C.

(57) ABSTRACT

An assembly for a drug delivery device is provided, the assembly having an actuator which is configured to perform a setting movement in a proximal direction in order to set a dose of a drug, and which is configured to perform a dispense movement in a distal direction in order to dispense a dose of a drug. The assembly further having a stop mechanism acting after a maximum amount of a drug has been delivered, which is configured to axially constrain the setting movement of the actuator such that the setting of a dose is inhibited, wherein a limited axial movement of the actuator is allowed.

12 Claims, 7 Drawing Sheets

(52) U.S. Cl.
CPC . *A61M 2205/581* (2013.01); *A61M 2205/582* (2013.01); *A61M 2205/583* (2013.01)

(58) Field of Classification Search
CPC .......... A61M 5/502; A61M 2005/3154; A61M 5/31541
See application file for complete search history.

(56) References Cited

U.S. PATENT DOCUMENTS

| | | |
|---|---|---|
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0142789 A1 | 6/2007 | Fisher et al. |
| 2009/0275916 A1 | 11/2009 | Harms et al. |
| 2010/0094205 A1* | 4/2010 | Boyd ................ A61M 5/31595 604/68 |

FOREIGN PATENT DOCUMENTS

| | | |
|---|---|---|
| EP | 0937476 | 8/1999 |
| JP | H05-345024 A | 12/1993 |
| RU | 2270698 C2 | 2/2006 |
| WO | 99/38554 | 8/1999 |
| WO | 01/10484 | 2/2001 |
| WO | 01/95959 A1 | 12/2001 |
| WO | 03/020347 | 3/2003 |
| WO | 2003/020347 A2 | 3/2003 |
| WO | 20081058665 | 5/2008 |
| WO | WO 2009/132777 | 11/2009 |
| WO | 2012/045793 | 4/2012 |

OTHER PUBLICATIONS

Russian Office Action for RU Application No. 2015142664, dated Mar. 7, 2018.

Japanese Office Action for JP App. No. 2015-562053, dated Dec. 19, 2017.

* cited by examiner

ASSEMBLY FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2014/054521 filed Mar. 10, 2014, which claims priority to European Patent Application No. 13158512.7 filed Mar. 11, 2013. The entire disclosure contents of these applications are herewith incorporated by reference into the present application.

TECHNICAL FIELD

The present disclosure relates to an assembly for a drug delivery device. In particular, the disclosure relates to pen-type drug delivery devices.

BACKGROUND

Pen-type drug delivery devices are used for injections by persons without formal medical training. This is increasingly common for self-treatment among patients having diabetes or the like. Such self-treatment enables patients to effectively manage their disease. Pen-type drug delivery devices usually comprise a housing in which a drive mechanism is located. Some kinds of drug delivery devices also comprise a compartment to accommodate a cartridge in which the drug is contained. By means of the drive mechanism, a piston in the cartridge is displaced such that the drug accommodated therein is dispensed through a needle.

Prior to injection, the required dose of a drug is set by means of a dose setting mechanism. Common designs of dose setting mechanisms comprise a number of tubular or sleeve-like elements such as a dose dial sleeve, a dose indicating sleeve, a drive sleeve or a ratchet sleeve. Such sleeves are often accommodated within and connected to each other.

A drug delivery device and an assembly for a drug delivery device are described for example in document WO 2008/058665 A1.

SUMMARY

It is an object of the present invention to provide an assembly for a drug delivery device having improved properties.

According to one aspect of the invention, an assembly for a drug delivery device is provided. The assembly comprises an actuator, which is configured to perform a setting movement in a proximal direction in order to set a dose of a drug, and which is configured to perform a dispense movement in a distal direction in order to dispense a dose of a drug. The assembly further comprises a stop mechanism acting after a maximum amount of a drug has been delivered, which is configured to axially constrain the setting movement of the actuator such that the setting of a dose is inhibited, wherein a limited axial movement of the actuator is allowed. The limited axial movement may be greater than zero, but less than a dose setting movement.

The maximum amount may be an amount of a drug which is available in the device. For example, the maximum amount may be an amount contained by a cartridge. According to one embodiment, the axial movement of the actuator may be limited after a determined number of dispense movements. In particular, the axial movement of the actuator may be limited after a last possible dose has been dispensed.

The advantage of a stop mechanism which inhibits the setting of a dose when a limited axial movement of the actuator is allowed is that no dose may be set even if a limited movement of the actuator is possible, for example due to manufacturing tolerances. Thereby, no wrong dose, for example an insufficient dose, may be dispensed by a user. In particular, a user may be inhibited from setting a dose which is larger then a remaining amount of a drug in the device. Thereby, the dosing accuracy may be improved. Furthermore, a feedback is given to a user that the device is empty. Additionally, the device may be locked by the stop mechanism. This is advantageous with disposable drug delivery devices which cannot be reused.

According to one embodiment, the actuator may be a button. The setting movement of the actuator may be a translational movement in a proximal direction. In particular, the actuator may be moved in a proximal direction by a user. In particular, the actuator may be moved in a proximal direction until it reaches a mechanical stop. The dispense movement of the actuator may be a movement in a distal direction, for example a purely axial movement. In particular, the actuator may be pushed in a distal direction by a user in order to dispense a dose. The actuator may be axially moveable and rotationally fixed with respect to the main housing part.

According to one embodiment, the assembly may comprise a main housing part, wherein the actuator may be configured to be depressed towards the main housing part in order to dispense a dose of a drug. In particular, the actuator may be depressed towards the main housing part until it abuts a mechanical stop at the end of a dispense operation.

The distal direction may be a direction towards a dispensing end of the device. Analogously, the distal end of the assembly or of any component may be and end which is nearest to the dispensing end. The proximal direction may be a direction away from a dispensing end of the device. The proximal end of the assembly or of any component may be an end which is furthest away from the dispensing end.

According to one embodiment, the assembly comprises a piston rod. The piston rod may be configured as a lead screw. During a dispensing movement of the actuator, the piston rod may perform an axial and rotational movement in a distal direction. Thereby, a dose of a drug may be dispensed. During the setting of a dose, the piston rod may be fixed with respect to the main housing part of the assembly. During the operation of the device, the piston rod may move from a start position to an end position. The piston rod may be in a start position when no dose has been delivered from the device. The start position may be a most proximal position of the piston rod. The end position may be a most distal position of the piston rod. The piston rod may be moved towards its end position by a movement of the actuator in a dose dispensing direction. The piston rod may be in an end position, when the maximum amount of a drug has been delivered, in particular when a last dose has been delivered.

According to one embodiment, the assembly may comprise an internal housing. The internal housing may be fixed to the main housing. The internal housing may comprise an opening, wherein the piston rod extends through the opening. Preferably, the piston rod is in threaded engagement with the internal housing.

The piston rod may comprise at least one last dose stop. The last dose stop may be configured as a protrusion of the piston rod. In one embodiment, the last dose stop may comprise two protrusions which are oppositely disposed.

The last dose stop may be arranged at a proximal section or near the proximal end of the piston rod.

The stop mechanism may comprise at least one stop element which is configured to interact with the at least one last dose stop of the piston rod. In particular, the stop element may be configured to abut the last dose stop. The assembly may be configured such that the stop element may interact with the last dose stop after a maximum amount of a drug has been dispensed. When the stop element abuts the last dose stop, a movement of the actuator in a proximal direction is inhibited. Thereby, the setting of a further dose is inhibited.

When a maximum amount, in particular a last dose of a drug has been delivered, the stop element may be arranged with an axial distance to the last dose stop. Furthermore, the last dose stop may be located directly above the stop element, seen from the dispensing end of the device. The amount of the axial distance between the stop element and the last dose stop corresponds to the possible limited axial movement of the actuator.

According to one embodiment, the last dose stop is formed such that it at least partially encompasses the stop element when the stop element abuts the last dose stop. Thereby, the device may be locked. According to one embodiment, the last dose stop may comprise insertion chamfers. The insertion chamfers may provide an abutment with respect to both possible turning directions of the piston rod. In particular, the chamfers may be inclined with respect to a longitudinal axis of the device. For example, the last dose stop may comprise the form of a pocket. The stop element may engage into the pocket. Thereby, a movement of the stop element laterally past the last dose stop may be inhibited. For example, the last dose stop may comprise the form of a cone or may be tapered. The stop feature may be formed accordingly such that it fits into the last dose stop.

According to one embodiment, the assembly comprises a drive member. The drive member may be a sleeve member. The drive member may be rotationally fixed with respect to the housing of the assembly. During the setting of a dose, the drive member may perform a relative axial movement with respect to the piston rod. The drive member may be configured to be moved along the piston rod in a proximal direction in order to set a dose. The dose may be a fixed dose. In particular, a user may not adjust the amount of a set dose. During the dispensing of a dose, the drive member may drive the piston rod towards a dispensing end of the device, i.e. particular towards end position. In particular, a movement of the drive member in a distal direction may cause the piston rod to rotate and move axially towards the distal end of the device. The amount of the axial movement of the drive member during the setting and the dispensing of a dose may be determined. Thereby, an amount of a set dose is fixed. For example, the assembly may comprise stop surfaces, wherein a further axial movement in one direction is inhibited when the drive member abuts a stop surface. The stop surfaces may be comprised by the housing. In particular, the drive member may perform an axial, non-rotational movement during the setting and the dispensing of a dose. The drive member may be arranged concentrically around the piston rod. Furthermore the drive member may comprise a tread at its internal surface. Thereby, the drive member may be in threaded engagement with a corresponding thread of the piston rod. The corresponding thread may be arranged at the proximal end of the piston rod.

When the actuator is pushed by a user in order to set a dose, drive member may be moved in a distal direction and exerts an axial force on the piston rod. Thereby, the piston rod may be caused to rotate through the opening of the internal housing. In addition, the piston rod also helically retracts partially back into the drive member.

Thereby, the axial displacement of the drive member during the dispensing of a dose is larger than the axial displacement of the piston rod during the dispensing of a dose. Thereby, a mechanical advantage may be achieved. The mechanical advantage may be adjusted by choosing the pitch of the threads of the drive member and the piston rod accordingly.

The stop element may be arranged at an internal surface of the drive member. For example, the stop element may be a protrusion at the internal surface of the drive member. According to one embodiment, the drive member may comprise two stop elements, in particular two protrusions at its internal surface which are oppositely disposed. The two protrusions of the drive member may interact with the two protrusions of the last dose stop.

According to one embodiment, the drive member may be coupled to the actuator such that a movement of the drive member causes a movement of the actuator and vice versa. For example, when a user pulls the actuator in order to set a dose, the drive member may be pulled in a proximal direction. When a user pushes the actuator in order to dispense a dose, the drive member may be pushed in a distal direction. According to one embodiment, the drive member and the actuator may be formed as one piece.

According to one embodiment, the assembly comprises a guiding feature. In particular, the guiding feature may be comprised by the piston rod. The guiding feature and the stop element may be configured to interact such that an unintentional rotation of the piston rod is inhibited during the setting of a dose. In particular, an unintentional rotation of the piston rod may be inhibited when a torque is exerted on the piston rod by the drive member during the setting of a dose. In particular, the guiding feature and the stop element may abut each other during the setting of a dose. Thereby, the dosing accuracy may be improved. During the dispensing of a dose, a rotation of the piston rod may be enabled.

According to one embodiment, the guiding feature and the stop element are configured to move past one another during the dispensing of a dose. In particular the rotation of the piston rod during the dispensing of a dose may be such that the guiding element does not abut the stop element. The stop element may move relative to the piston rod along a helical path.

According to one embodiment, the guiding feature may comprise a plurality of splines. The splines may be arranged in at least one row, which extends along the piston rod in an axial direction. According to one embodiment, the piston rod may comprise three rows of splines. The rows may be equally distributed around an outer circumference of the piston rod.

During the setting of a dose, the stop element may abut at least one of the splines of the guiding feature. In particular, the stop element may abut two splines which are arranged above another in an axial direction. The distance between the two splines may be less than an axial extension of the stop element. Thereby, a rotation of the piston rod may be reliably inhibited during the setting of a dose. However, the stop element does not abut a spline at the very beginning and the very end of the dose setting.

According to a further aspect of the invention, a drug delivery device is provided. The drug delivery device comprises a drive assembly as previously described.

The drug delivery device may be an injection device, in particular a pen-type device. The drug delivery device may be suited to deliver a dose of a drug to a user. A dose may be delivered by depressing the actuator. The drug delivery device may be a fixed dose device such that a user cannot select the size of a dose. For example, the dose setting mechanism may be a pull-push mechanism. The drug delivery device may be configured for multiple dose applications. The drug may be delivered to a user by means of a needle. The device may be delivered to a user in a fully assembled condition ready for use. In particular, the device may be prefilled. The drug delivery device may be a disposable device. The term "disposable" means that the drug delivery device cannot be reused after an available amount of a drug has been delivered from the drug delivery device. Alternatively, the drug delivery device may be a reusable device. The drug delivery device may be configured to deliver a liquid drug. The drug may be, for example, insulin.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(02)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, refinements and expediencies become apparent from the following description of the exemplary embodiments in connection with the figures.

DETAILED DESCRIPTION

Figure 1:
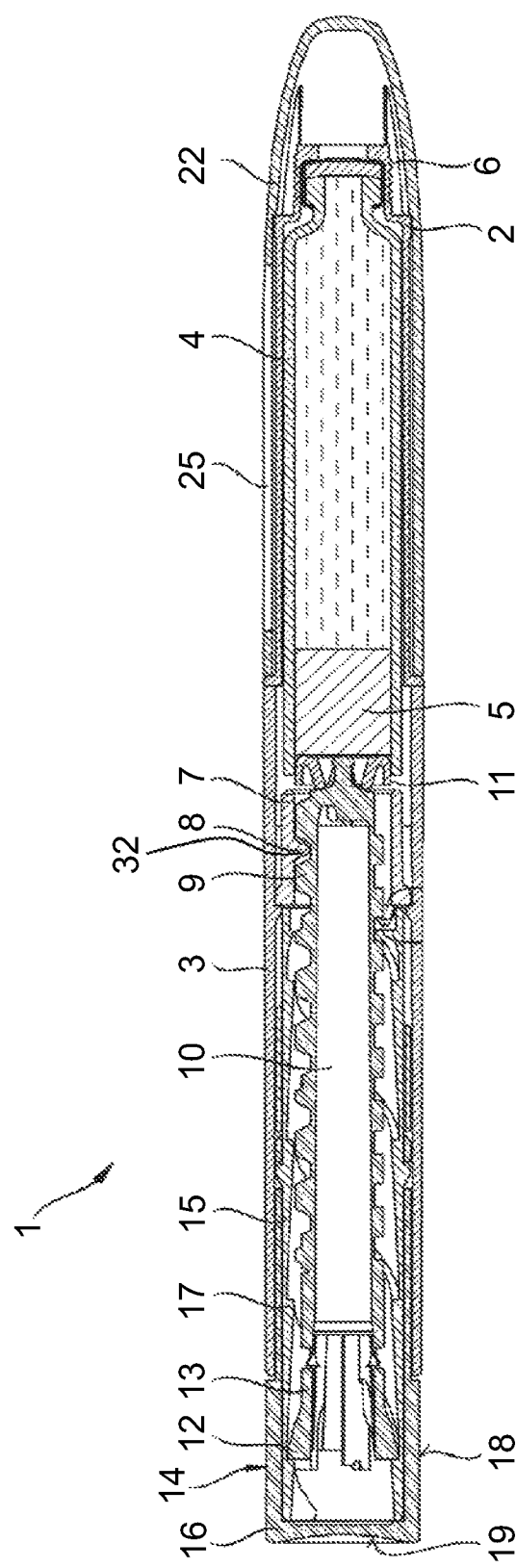
FIG. 1 shows a sectional view of a drug delivery device.

FIG. 1 shows a sectional view of a drug delivery device 1. The drug delivery device 1 comprises a cartridge retaining part 2, and a main housing part 3. The proximal end of the cartridge retaining part 2 and the distal end of the main housing 3 are secured together by any suitable means known to the person skilled in the art. In the illustrated embodiment, the cartridge retaining part 2 is secured within the distal end of the main housing part 3.

A cartridge 4 from which a number of doses of a medicinal product may be dispensed is provided in the cartridge retaining part 2. A piston 5 is retained in the proximal end of the cartridge 4.

A removable cap 22 is releasably retained over the distal end of the cartridge retaining part 2. The removable cap 22 is optionally provided with one or more window apertures 25 through which the position of the piston 5 within the cartridge 4 can be viewed.

The distal end of the cartridge retaining part 2 in the illustrated embodiment is provided with a distal threaded region 6 designed for the attachment of a suitable needle assembly (not shown) to enable medicament to be dispensed from the cartridge 4.

In the illustrated embodiment, the main housing part 3 is provided with an internal housing 7. The internal housing 7 is secured against rotational and axial movement with respect to the main housing part 3. Alternatively, the internal housing 7 may be formed integrally with the main housing part 3. The internal housing 7 is provided with a circular opening 8. A thread 32 is arranged at the opening 8 of the internal housing 7. In particular, the internal housing 7 is configured as a piston rod nut. In the illustrated embodiment the circular opening 8 comprises a series of part threads rather than a complete thread.

A first thread 9 is formed at the distal end of the piston rod 10. The piston rod 10 is of generally circular cross-section. The first thread 9 of the piston rod 10 extends through and is threadedly engaged with the thread 32 of the circular opening 8 of the internal housing 7. A pressure foot 11 is located at the distal end of the piston rod 10. The pressure foot 11 is disposed to abut the proximal face of the piston 5. A second thread 12 is formed at the proximal end of the piston rod 10. In the illustrated embodiment the second thread 12 comprises a series of part threads, rather than a complete thread, formed on flexible arms 13 of the piston rod 10.

The first thread 9 and the second thread 12 are oppositely disposed.

In the illustrated embodiment the first thread 9 is provided with a plurality of features (see FIG. 2) that cooperate with the thread 32 of the circular opening 8 to prevent movement of the piston rod 10 in the proximal direction during setting of the dose. In particular, the piston rod 10 is back-winding restrained.

A drive member 14 extends about the piston rod 10. The drive member 14 is configured as a drive sleeve. The drive member 14 comprises a threaded part 15 of a generally cylindrical cross-section. An actuator 16 is located at a proximal end of the drive member 14. The threaded part 15 and the actuator 16 are secured to each other to prevent rotational and/or axial movement there between. Alternatively, the drive member 14 may be a unitary component consisting of an integrated threaded part 15 and actuator 16. During the setting of a dose, the drive member 14 is moved in a proximal direction. In particular, a user may pull the actuator 16 in a proximal direction out of the main housing part 3.

In the illustrated embodiment, the threaded part 15 is provided with a longitudinally extending helical thread 17 formed on the internal cylindrical surface. The flank of the proximal side of the helical thread 17 is designed to maintain contact with the second thread 12 of the piston rod 10 when dispensing a dose, whilst the flank of the distal side of the helical thread 17 is designed to allow the second thread 12 of the piston rod 10 to disengage when setting a dose. In this way the helical thread 17 of the threaded part 15 is releasably engaged with the second thread 12 of the piston rod 10.

The drive member 14 has a plurality of features formed on the external surface designed to move axially within the guide slots of the main housing 3. These guide slots define the extent of permissible axial movement of the drive member 14 with respect to the housing part 3. In the illustrated embodiment the guide slots also prevent rotational movement of the drive member 14 relative to the main housing part 3.

The actuator 16 has a plurality of grip surfaces 18 and a dispensing face 19.

To increase intuitiveness of the operation of the device, the main housing part 3 may be provided with a window aperture through which graphical status indicators, provided on the drive member 14, can be viewed.

An operation of the drug delivery device in accordance with the present invention will now be described.

To set a dose a user grips the grip surfaces 18 of the drive member 14. The user then pulls the drive member 14 in a proximal direction away from the main housing part 3.

The piston rod 10 is prevented from moving proximally by the thread 32 of the circular opening 8 of the internal housing 7 interacting with thread features on the first thread 9 of the piston rod 10 or by any other suitable means. In particular, the first thread 9 and the second thread 12 of the piston rod 10 axially and rotationally constrain the piston rod 10 as long as the relative position of the internal housing 7 and the drive sleeve 14 is maintained. As the drive member 14 travels in the proximal direction relative to the piston rod 10 during the setting of a dose, the second thread 12 of the piston rod 10 is displaced radially inwards by the flank of the distal side of helical thread 17 of the drive member 14.

The proximal travel of the drive member 14 is limited by the guide slots (not shown) of the internal housing 7 or of the main housing 3 to a distance corresponding to essentially one thread pitch of the helical thread 17 of the drive member 14. At the end of the travel of the drive member 14, the second thread 12 of the piston rod 10 engages with the helical thread 17 under the action of the flexible arms 13 of the piston rod 10. By this action the drive member 14 is displaced a distance essentially equal to one pitch of the helical thread 17 of the drive member 14 in the proximal direction relative to the piston rod 10. The action of the second thread 12 positively engaging the helical thread 17 of the drive member 14 under a force provided by the flexible arms 13 creates an audible and tactile feedback to the user to indicate that the dose has been set. Additionally, visual feedback regarding dose setting may be indicated by an optional graphical status indicator, provided on the drive member 14, which can be viewed through an optional window aperture in the main housing part 3.

When the dose has been set, the user may then dispense this dose by depressing the dispensing face 19 of the actuator 16. By this action the drive member 14 is moved axially in the distal direction relative to the main housing part 3. As the second thread 12 of the piston rod 10 is positively engaged with the helical thread 17 of the drive member 14 the piston rod 10 is caused to rotate with respect to the internal housing 7 by the axial movement of the drive member 14 in the distal direction. As the piston rod 10 rotates, the first thread 9 of the piston rod 10 rotates within the threaded circular opening 8 of the internal housing 7 causing the piston rod 10 to move axially in the distal direction with respect to the internal housing 7.

In addition to advancing, the piston rod 10 also helically retracts partially back into the drive member 14. Thereby, the axial displacement of the drive member 14 is larger than the axial displacement of the piston rod 10.

The distal axial movement of the piston rod 10 causes the pressure foot 11 to bear against the piston 5 of the cartridge 4 causing a dose of medicament to be dispensed through an attached needle.

The distal travel of the drive member 14 is limited by the guide slots or by a stop surface (not shown) of the internal housing 7. Visual feedback regarding dose dispensing may be indicated by an optional graphical status indicator, provided on the drive member 14, which can be viewed through an optional window aperture in the main housing part 3.

Further doses may be delivered as required up to a pre-determined maximum number of doses.

Figure 2:
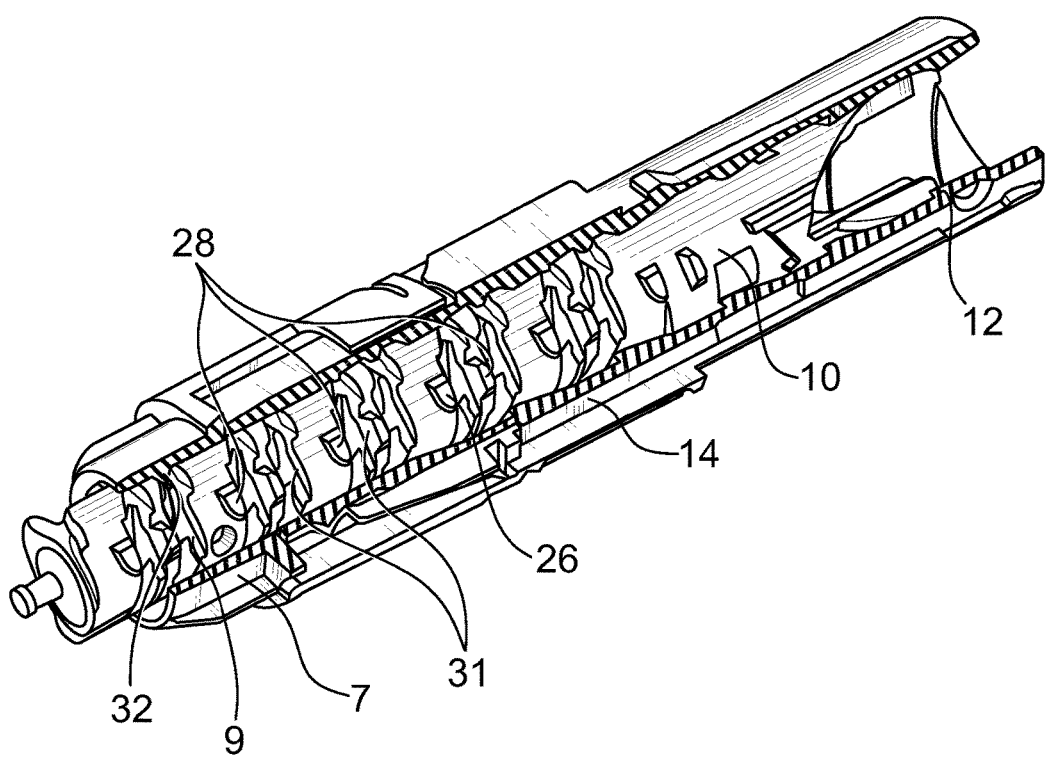
FIG. 2 shows an assembly of the drug delivery device.

The piston rod 10, the drive member 14 and the internal housing 7 are shown in a more detailed view in FIG. 2.

The first thread 9 of the piston rod 10 has flat portions 31. During the setting of a dose, the thread 32 of the internal housing 7 interacts with the flat portions 31. The interaction of the internal housing 7 with the flat portions 31 of the piston rod 10 is configured to axially constrain the piston rod 10 during the setting of a dose. In particular, the piston rod 10 is prevented from moving in a proximal direction together with the drive sleeve 14 during the setting of a dose. In an alternative embodiment, the first thread 9 of piston rod 10 may have a shallow pitch, such that the interface between the piston rod 10 and the internal housing 7 would be non-overhaulable.

Figure 3:
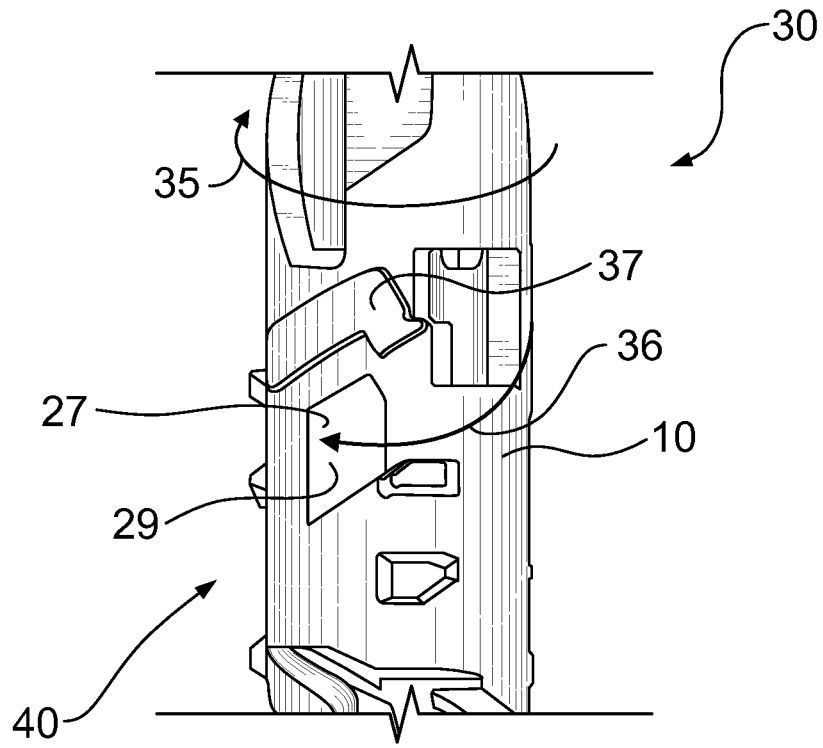
FIGS. 3 and 4 show the stop mechanism in different states.
Figure 4:
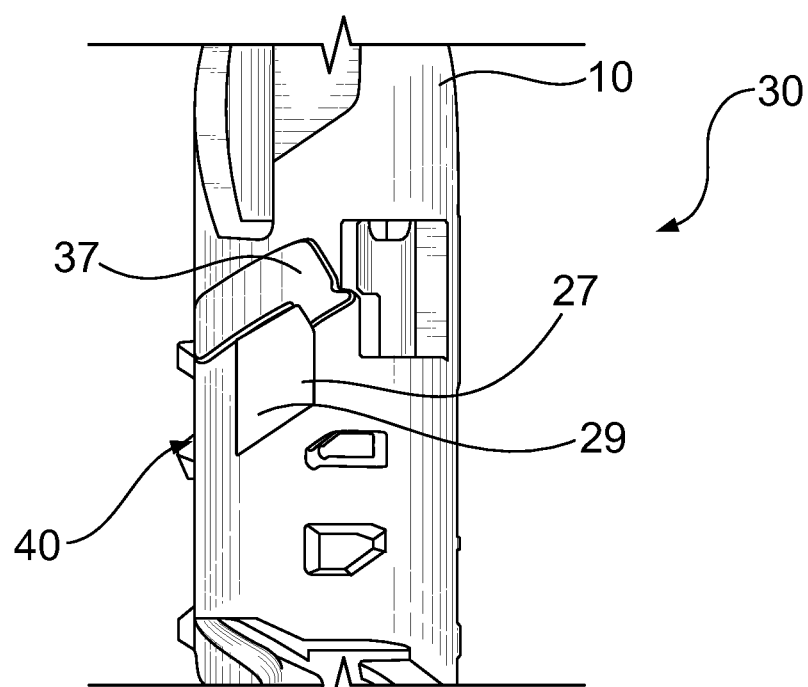

FIGS. 3 and 4 show a stop mechanism 40 of the assembly 30. The stop mechanism 40 is configured to inhibit the setting of a dose after an available amount of a drug has been dispensed from the device. In particular, the stop mechanism 40 inhibits the setting of a dose when the cartridge 4 is empty In particular, the stop mechanism 40 gives a feedback to a user that the device is empty. For example 15 doses of a drug may be delivered from the device 1. The setting of a sixteenth dose may be inhibited.

Figure 5:
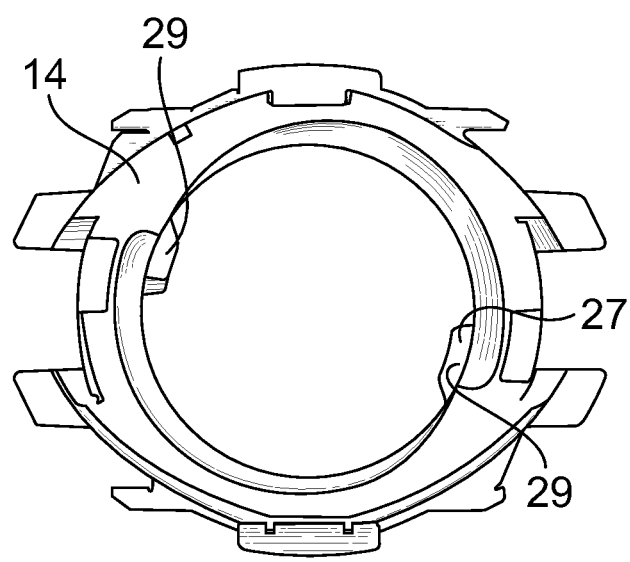
FIG. 5 shows the drive member in a top view.

The stop mechanism comprises a stop element 27. The stop element 27 is an integral part of the drive member 14 and has a proximally facing stop surface 27a and a transverse facing stop surface 27b (see FIG. 3). A last dose stop 37 radially protrudes outward from piston rod 10 and has a distally facing stop surface 37a. As shown in FIG. 5, the stop element 27 is configured as a protrusion 29 on an internal surface of the drive member 14. In particular, the stop element 27 comprises two protrusions 29. The two protrusions 29 are oppositely disposed. The second protrusion 29 of the stop element 27, which is arranged oppositely to the first protrusion 29, adds radial stability to the mechanism. Furthermore, the drive member 14 may be a symmetrical component. The stop element 27 is arranged at a distal section of the drive member 14.

In FIGS. 3 and 4, the drive member 14 is cut away for clarity reasons except from the protrusion 29.

By means of the stop mechanism 40, an axial movement of the drive member 14 in a proximal direction is constrained. In particular, an axial movement of the drive member 14 is constrained after a last dose has been dispensed from the device. Thereby, an axial movement of the actuator 16 is also constrained. Yet, a limited axial movement of the drive member 14 and the actuator 16 is still possible. Such a movement may be greater than zero, but less than a regular dose setting movement. The limited axial movement may be possible due to manufacturing tolerances.

In FIG. 3, the assembly 30 is shown in a state when a last dose has been dispensed. The piston rod 10 comprises a last dose stop 37. The last dose stop 37 is configured as a protrusion on the piston rod 10. In one embodiment, the last dose stop 37 may comprise two protrusions which are oppositely disposed on the piston rod 10.

When a last dose has been dispensed, the last dose stop is arranged above the stop element 27, seen from a dispensing end of the assembly. Furthermore, the last dose stop 37 is arranged with an axial distance to the stop element 27. When a user now tries to set a dose by pulling the actuator 16, the drive member 14 moves in a proximal direction and the stop element 27 abuts the last dose stop 37 of the piston rod 10, as shown in FIG. 4. When the stop element 27 abuts the last dose stop 37, no further movement of the drive member 14 in a dose setting direction is possible. The last dose stop 37 is formed such that it at least partially encompasses the stop member 27. For example, the protrusion of the last dose stop 37 comprises the form of a pocket. Thereby, a relative rotation of the drive member 14 and the piston rod 10 is inhibited if a user forcibly pulls the actuator 16 after the stop element 27 has abutted the last dose stop 37.

Figure 6:
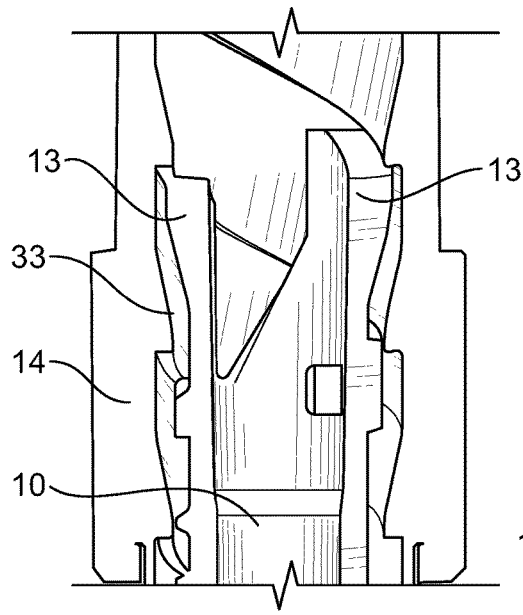
FIGS. 6 and 7 show a sectional view of the piston rod and the drive member.
Figure 7:
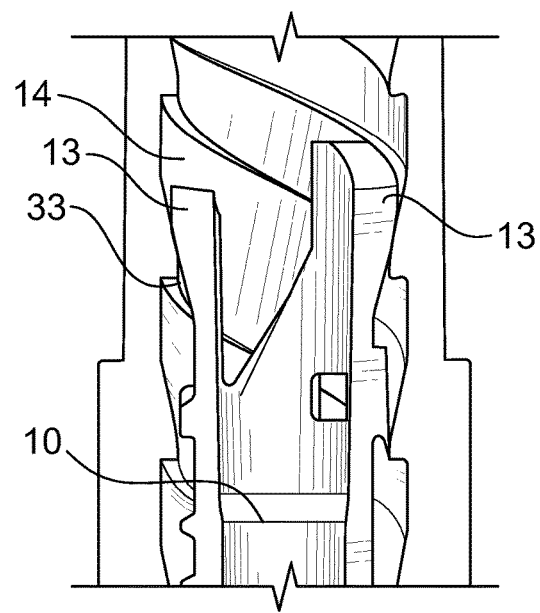

FIGS. 6 and 7 show a sectional view of the drive member 14 and the piston rod 10.

FIG. 6 shows the piston rod 10 and the drive member 14 in a state when a dose has been set or before the setting of a dose. In particular, the helical thread 17 of the drive member 14 is engaged with the second thread 12 of the piston rod 10. FIG. 7 shows the piston rod 10 and the drive member 14 during the setting of a dose. During the setting of a dose, the helical thread 17 of the drive member 14 is not engaged with the second thread 12 of the piston rod 10.

The drive member 14 comprises ramped surfaces 33. The ramped surfaces 33 slide over the flexible arms 13 of the piston rod 10 during the setting of a dose, as shown in FIG. 7. The force applied to the flexible arms 13 of the piston rod 10 by the ramped surfaces 33 induces a torque on the piston rod 10.

In order to prevent the piston rod 10 from rotating during the setting of a dose, piston rod 10 comprises a guiding feature 26. The guiding feature 26 is configured to interact with the stop element 27 during the setting of a dose.

The guiding feature 26 of the piston rod 10 is shown in FIGS. 2 to 4 and in FIGS. 8 to 11. The guiding feature 26 comprises a plurality of splines 28. The splines 28 are arranged in a row with a distance to each other. In particular, the guiding feature 26 comprises three rows (not shown) of splines 28. The three rows are equally distributed around the outer circumference of the piston rod 10.

Figure 8:
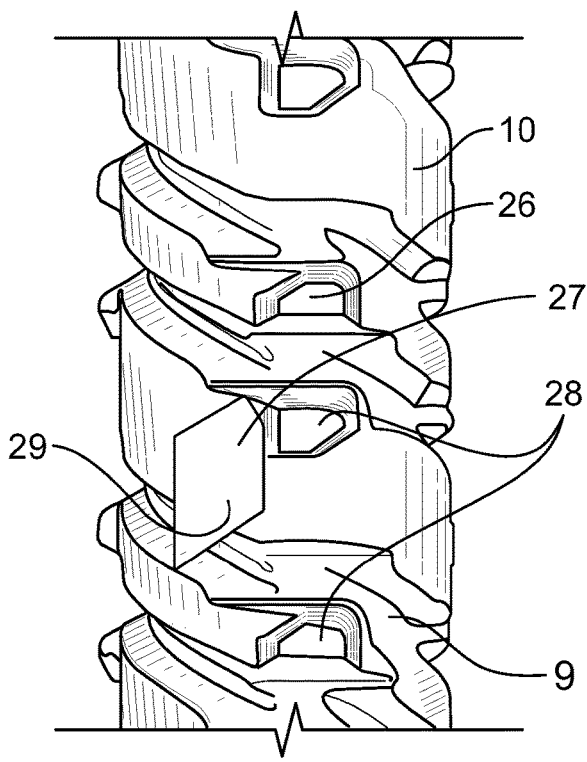
FIGS. 8 and 9 show the guiding feature and the stop element in different states.

FIG. 8 shows a section of the piston rod 10 and one protrusion 29 of the stop element 27. In particular, FIG. 8 shows a state during the setting of a dose. The drive member 14 is cut away for clarity reasons except from the protrusion 29. During the setting of a dose, the stop element 27 of the drive member 14 abuts the guiding feature 26 of the piston rod 10. Thereby, the piston rod 10 is inhibited from rotating. The abutment of the drive member 14 and the guiding feature 26 results from the torque which is induced on the piston rod 10 during the setting of a dose. The direction of the torque which is applied to the piston rod 10 is indicated by arrow 35.

The stop element 27 may pass two or more splines 28 during one setting movement. The axial distance of these splines 28 is less than an axial extension of the stop element 27. Thereby, the stop element 27 may not pass between two splines 28 during the setting of a dose. The splines 28 are arranged directly adjacent to the first thread 9 of the piston rod 10.

Figure 9:
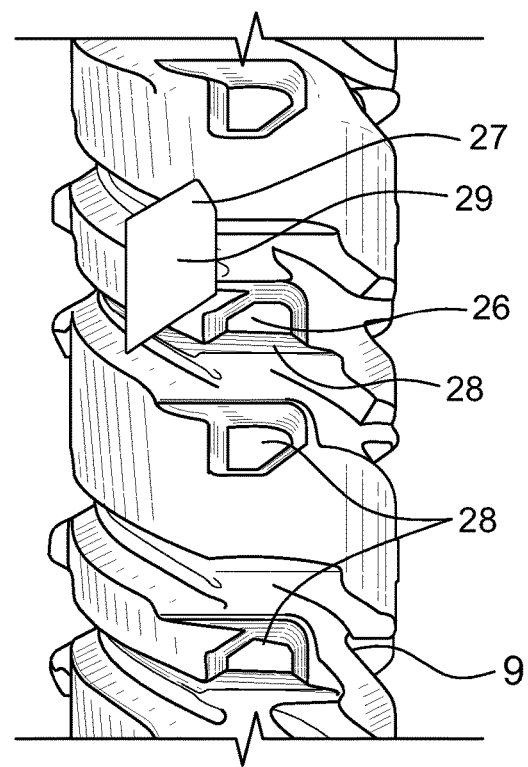

FIG. 9 shows the piston rod 10 and the protrusion 29 of FIG. 8 in a state when a dose has been set. In this state, the stop element 27 does not abut the guiding feature 26 anymore.

During the dispensing of a dose, the piston rod 10 rotates with respect to the drive member 14. During this rotation, the stop element 27 performs a helical movement along the piston rod 10. In particular, the protrusions 29 of the stop element 27 move through between the spline features 28 of the guiding feature. The helical movement of the stop element is indicated by arrow 36 in FIG. 3.

Figure 10:
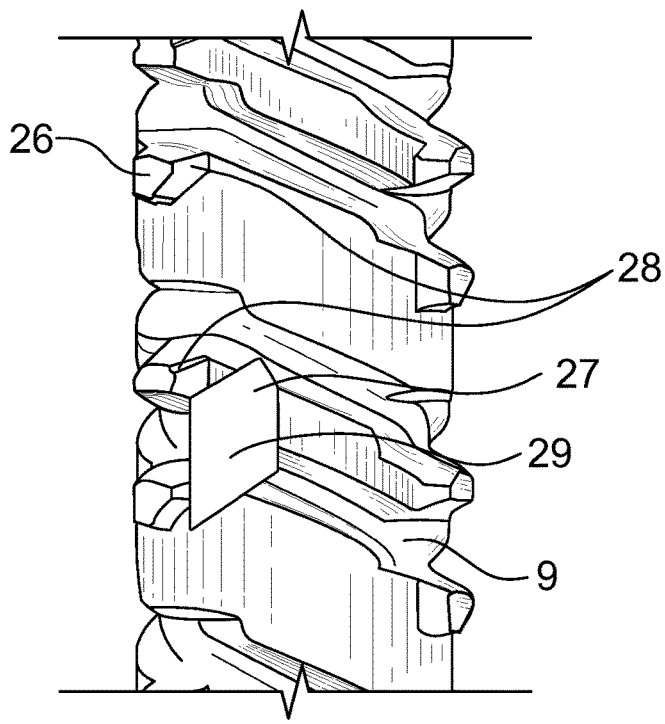
FIGS. 10 and 11 show the states of FIGS. 8 and 9 from a different view.
Figure 11:
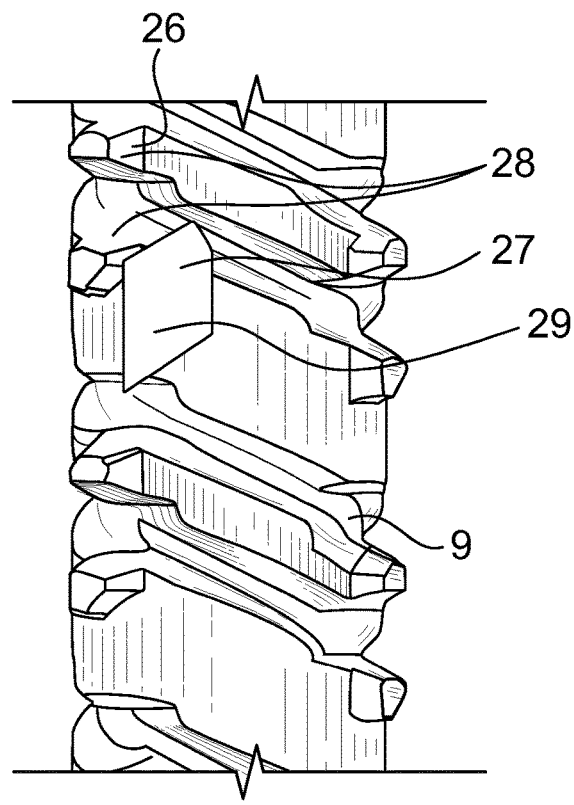

FIGS. 10 and 11 show the second protrusion 29 of the stop element 27 and the piston rod during the setting of a dose and after the setting of a dose, analogously to FIGS. 8 and 9.

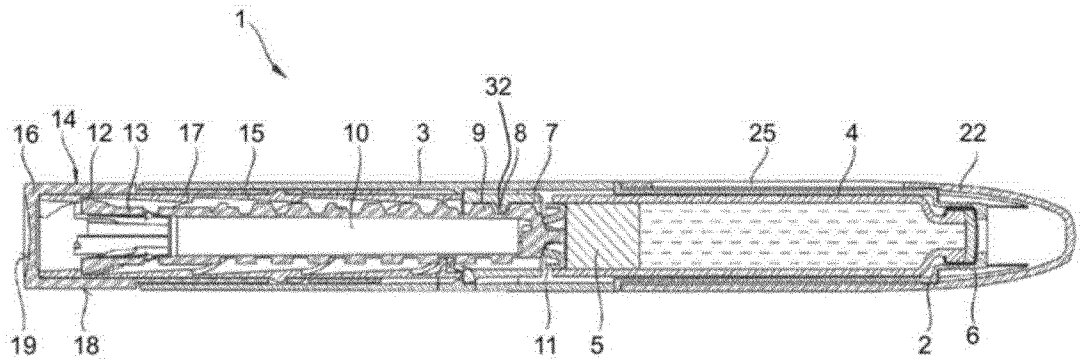

The invention claimed is:

1. An assembly for a drug delivery device, comprising:
an actuator which is configured to perform a setting movement in a proximal direction in order to set a dose of a drug, and which is configured to perform a dispense movement in a distal direction in order to dispense a dose of a drug;
a piston rod comprising a last dose stop that protrudes radially outward from an outer surface of the piston rod and has a distally facing stop surface; and
a drive member which is configured to be moved along the piston rod in a proximal direction during dose setting and is configured to drive the piston rod in a distal direction during the dispensing of a dose, where the drive member further comprises two identical stop elements each protruding radially inward from an internal surface of the drive member and oppositely disposed, where each stop element has a proximally facing stop surface and transverse facing stop surface,
wherein the proximally facing stop surface prevents setting of a dose after a maximum amount of a drug has been delivered by abutting the distally facing surface of the last dose stop to axially constrain the setting movement of the actuator such that the setting of a dose is inhibited, wherein a limited axial movement of the actuator is allowed,
wherein the transverse facing stop surface prevents rotation of the piston rod during dose setting by abutting a guiding feature on the piston rod, where the guiding feature enables rotation of the piston rod during the dispensing of a dose.

2. An assembly for a drug delivery device, comprising
an actuator which is configured to perform a setting movement in a proximal direction in order to set a dose of a drug, and which is configured to perform a dispense movement in a distal direction in order to dispense a dose of a drug,
a stop mechanism acting after a maximum amount of a drug has been delivered, and which is configured to axially constrain the setting movement of the actuator such that the setting of a dose is inhibited, wherein a limited axial movement of the actuator is allowed,
a piston rod wherein the piston rod comprises a last dose stop, and wherein the stop mechanism comprises a stop element, the stop element comprising a protrusion, wherein a movement of the actuator in a proximal direction is inhibited when the protrusion abuts the last dose stop;
a drive member which is configured to be moved along the piston rod in a proximal direction in order to set a dose, wherein the drive member is configured to drive the piston rod towards a dispensing end of the device during the dispensing of a dose, the drive member being coupled to the actuator such that a movement of the drive member causes a movement of the actuator and vice versa, wherein the stop element is arranged at an internal surface of the drive member, wherein the piston rod comprises a guiding feature,
wherein the guiding feature comprises a plurality of splines that are arranged at a distance above one another in an axial direction,
wherein the guiding feature and the protrusion of the stop element are configured to interact such that a rotation of the piston rod is inhibited during the setting of a dose and a rotation of the piston rod is enabled during the dispensing of a dose,
wherein during the setting of a dose the protrusion of the stop element abuts two splines of the guiding feature, where the two splines are arranged above one another in an axial direction and the distance between the two splines is less than an axial extension of the protrusion of the stop element, and
wherein the guiding feature also comprises two further splines wherein the distance between the two further splines is greater than the axial extension of the protrusion of the stop element.

3. The assembly according to claim 2, wherein the last dose stop has the form of a pocket which at least partially encompasses the stop element.

4. The assembly according to claim 2, wherein the guiding feature and the stop element abut each other during the setting of a dose.

5. The assembly according to claim 2, wherein the guiding feature and the stop element are configured to move past one another during the dispensing of a dose.

6. The assembly according to claim 2, wherein the guiding feature comprises three rows of splines, which are equally distributed around an outer circumference of the piston rod.

7. The assembly according to claim 2, wherein the stop element is in contact with at least one spline of the guiding feature during the dose setting movement of the drive member.

8. The assembly according to claim 2, wherein the drive member performs an axial, non rotational movement during the setting and dispensing of a dose.

9. The assembly according to claim 2, wherein the axial movement of the drive member during the dispensing of a dose is larger than the axial movement of the piston rod during the dispensing of a dose.

10. The assembly according to claim 2, wherein a movement of the piston rod is inhibited during the setting of a dose.

11. The assembly according to claim 2, wherein a movement of the drive member in a distal direction towards a dispensing end of the device causes the piston rod to rotate and move axially towards a distal end of the device.

12. An assembly for a drug delivery device, comprising:
an actuator which is configured to perform a setting movement in a proximal direction in order to set a dose of a drug, and which is configured to perform a dispense movement in a distal direction in order to dispense a dose of a drug;
 a piston rod comprising a last dose stop that protrudes radially outward from an outer surface of the piston rod and has a distally facing stop surface; and
 a drive member which is configured to be moved along the piston rod in a proximal direction during dose setting and is configured to drive the piston rod in a distal direction during the dispensing of a dose, where the drive member further comprises a stop element protruding radially inward from an internal surface of the drive member, where the stop element has a proximally facing stop surface and a transverse facing stop surface,
wherein the proximally facing stop surface prevents setting of a dose after a maximum amount of a drug has been delivered by abutting the distally facing surface of the last dose stop to axially constrain the setting movement of the actuator such that the setting of a dose is inhibited, wherein a limited axial movement of the actuator is allowed,
wherein the transverse facing stop surface prevents rotation of the piston rod during dose setting by abutting a guiding feature on the piston rod, where the guiding feature enables rotation of the piston rod during the dispensing of a dose.

\* \* \* \* \*

UNITED STATES PATENT AND TRADEMARK OFFICE
CERTIFICATE OF CORRECTION

PATENT NO. : 10,201,663 B2
APPLICATION NO. : 14/770852
DATED : February 12, 2019
INVENTOR(S) : David Aubrey Plumptre and Robert Frederick Veasey It is certified that error appears in the above-identified patent and that said Letters Patent is hereby corrected as shown below:

On the Title Page

Under ABSTRACT "12 Claims, 7 Drawing Sheets" should read: --10 Claims, 7 Drawing Sheets-- as shown on the attached page In the Claims In Column 14, Line 50, delete Claim 4

In Column 14, Line 59, delete Claim 7

Signed and Sealed this
Fourteenth Day of February, 2023

Katherine Kelly Vidal
*Director of the United States Patent and Trademark Office*

(12) United States Patent
Plumptre et al.

(10) Patent No.: US 10,201,663 B2
(45) Date of Patent: Feb. 12, 2019

(54) ASSEMBLY FOR A DRUG DELIVERY DEVICE

(71) Applicant: SANOFI-AVENTIS DEUTSCHLAND GMBH, Frankfurt am Main (DE)

(72) Inventors: David Aubrey Plumptre, Worcestershire (GB); Robert Frederick Veasey, Warwickshire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 0 days.

(21) Appl. No.: 14/770,852

(22) PCT Filed: Mar. 10, 2014

(86) PCT No.: PCT/EP2014/054521
§ 371 (c)(1),
(2) Date: Aug. 27, 2015

(87) PCT Pub. No.: WO2014/139910
PCT Pub. Date: Sep. 18, 2014

(65) Prior Publication Data
US 2016/0008551 A1 Jan. 14, 2016

(30) Foreign Application Priority Data
Mar. 11, 2013 (EP) .................... 13158512

(51) Int. Cl.
A61M 5/315 (2006.01)
(52) U.S. Cl.
CPC .... *A61M 5/31541* (2013.01); *A61M 5/31555* (2013.01); *A61M 5/31585* (2013.01);
(Continued)

(58) Field of Classification Search
CPC ............ A61M 5/3146; A61M 5/31551; A61M 5/31595; A61M 5/31501; A61M 5/31528;
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

CN 102083487 6/2011
EP 0937471 8/1999
(Continued)

OTHER PUBLICATIONS

International Search Report for Int. App. No. PCT/EP2014/054521, completed Apr. 29, 2014.
(Continued)

*Primary Examiner* — Emily Schmidt
(74) *Attorney, Agent, or Firm* — Fish & Richardson P.C.

(57) ABSTRACT

An assembly for a drug delivery device is provided, the assembly having an actuator which is configured to perform a setting movement in a proximal direction in order to set a dose of a drug, and which is configured to perform a dispense movement in a distal direction in order to dispense a dose of a drug. The assembly further having a stop mechanism acting after a maximum amount of a drug has been delivered, which is configured to axially constrain the setting movement of the actuator such that the setting of a dose is inhibited, wherein a limited axial movement of the actuator is allowed.

10 Claims, 7 Drawing Sheets